United States Patent [19]

Gaafar

[11] 4,029,756

[45] June 14, 1977

[54] SEROLOGICAL PROCEDURE FOR DETERMINING PRESENCE OF NEISSERIA GONORRHOEAE ANTIBODIES

[75] Inventor: Hassan A. Gaafar, Slingerlands, N.Y.

[73] Assignee: Research Corporation, New York, N.Y.

[22] Filed: Nov. 26, 1975

[21] Appl. No.: 635,325

[52] U.S. Cl. ................... 424/1; 23/230 B; 195/103 S R; 252/301.1 R; 252/408; 252/301.16; 424/1.5; 424/12; 424/13; 424/92

[51] Int. Cl.² ............. A61K 43/00; A61K 39/02; G01N 31/00; G01N 33/16

[58] Field of Search ............ 424/1, 12, 13, 92, 1.5; 23/230 B; 252/408, 301.1 R, 301.2 R; 195/103.5 R

[56] References Cited

UNITED STATES PATENTS

| 3,577,527 | 5/1971 | Edwards | 424/92 |
|---|---|---|---|
| 3,636,192 | 1/1972 | Gotschlich | 424/92 |
| 3,859,434 | 1/1975 | Jennings et al. | 424/92 |
| 3,974,269 | 8/1976 | Maley | 424/1.5 |

FOREIGN PATENTS OR APPLICATIONS

| 2,343,264 | 3/1974 | Germany | 424/1 |

OTHER PUBLICATIONS

Reddick, Anne; Health Laboratory Science, vol. 12, No. 3. pp. 208–214 (July 1975).
Chemical Abstracts, vol. 83, p. 145646p, (1975), citing Carbonare, S., et al., Rev. Inst. Adolfo Lutz, vol. 34, pp. 119–125 (1974).
Chem. Abst., vol. 81, 2135u (1974), citing DeCecchini, G., et al., Rev. Asoc. Bioquim. Argent., vol 38, pp. 207–208. (1973).
Chem. Abst., vol. 81, 134532f (1974), citing Fr Patent 1,604,144, published 8/20/71.
Tramont, E. C., et al. J. Infect. Diseases, vol. 130, No. 3, pp. 240–247 (Sept. 74).
Welch, B.G., et al., J. Infect. Diseases, vol. 127, No. 1, pp. 68–76 (Jan. 1973).

Primary Examiner—Benjamin R. Padgett
Assistant Examiner—T. S. Gron
Attorney, Agent, or Firm—Copper, Dunham, Clark, Griffin & Morgan

[57] ABSTRACT

Enhancement of the specificity of the serological method for determining the presence of *Neisseria gonorrhoeae* antibodies in human serum by prior removal of cross reacting *Neisseria meningitidis* antibodies.

13 Claims, No Drawings

SEROLOGICAL PROCEDURE FOR DETERMINING PRESENCE OF NEISSERIA GONORRHOEAE ANTIBODIES

RELATED APPLICATIONS

The methods described herein are improvements over those described in copending applications Ser. No. 551,983 filed Feb. 21, 1975, now abandoned, Ser. No. 554,061, filed Feb. 28, 1975, now abandoned, Ser. No. 554,087 filed Feb. 28, 1975, now abandoned, Ser. No. 554,088 filed Feb. 28, 1975, now abandoned, Ser. No. 554,089 filed Feb. 28, 1975, now abandoned, Ser. No. 554,090 filed Feb. 28, 1975, now abandoned, Ser. No. 554,105 filed Feb. 28, 1975, now abandoned.

BACKGROUND OF THE INVENTION

Gonorrhea is currently the most common reportable disease in the United States and one of the major problems throughout the world. Several factors have been suggested as responsible for the pandemic, but it is generally accepted that the lack of a blood test suitable for mass screening may be the most important factor in the failure to control the disease. The above-identified applications describe procedures for serological testing based upon the discovery of the production of a *Nisseria gonorrhoeae* (N.g.) antigen which is heat labile and reacts with N.g. antibodies in human sera thereby to detect the presence of a current or past gonorrhea infection. The procedures have a high specificity rate which makes it acceptable as an adjunct diagnostic test for use in voluntary screening programs. However, the social and psychological reaction to a false positive in a mandated premarital test is so unfavorable that methods of high specificity are desired.

THE INVENTION

It has now been discovered that the risk of false positive reactions in serological testing for N.g. antibodies can be substantially reduced by first absorbing the sera to be tested with a *Neisseria meningitudes* (N.m.) sorben composition. This absorbent substantially removes from the sera any cross reacting antibodies which may be present. It has been discovered that approximately 60% of the false positive reactions may be due to the fact that N.g. antigenic compositions may give false positive results with sera containing m. antibodies which react with N.m.

The invention of this application will be best understood by considering it in the light of the inventions described and claimed in the above identified related applications.

In accordance with that description, it was discovered that N.g. organisms, especially ATCC 21823, 21824 and 21825, produce an antigen which is heat labile and reacts with antibodies in human sera produced in response to N.g. antigens thereby to indicate the presence of a current or past gonorrhea infection.

A number of procedures have been devised for utilizing the antigen to test for the presence of N.g. antibodies. The preferred test in an immunofluorescent test procedure utilizing suspensions of microorganisms. In the test, a suspension containing the antigen is prepared, incubated with two separate samples of sera and tested for the production of an antigen-antibody complex. One sample of serum is heated with the object of inactivating heat labile cross-reacting antibodies which may be present. The other sample is not subjected to heat. The key to the test is that antibodies caused by a gonorrhea infection are heat stable whereas the cross-reacting antibodies are heat labile. Therefore, a positive reaction with both of the test samples is a clear indication of the presence of N.g. stimulated antibodies. A negative reaction in both specimens is a clear indication of the absence of such antibodies. A negative reaction with the heated sample coupled with a positive reaction with the unheated sample is an indication of the presence of natural antibodies.

The formation of a positive antigen-antibody complex can be detected by any of the presently available methods. Generally, the procedure is to incubate the complex with a labeled anti-human immunoglobulin, preferably immunoglobulin G (IgG). The heavy chain IgG is preferred. The immunoglobulin can be labeled, for example, with a detectable radioactive element, an enzyme or a chemical which fluoresces when exposed to ultraviolet or other specified light.

In one method, separate samples of the antigen containing suspension are placed on a slide and incubated with the sera under test, one sample of which is heated, the other unheated. The thus prepared separate specimens are then incubated with an anti-human IgG labeled with fluorescent material such as fluorescein, rhodamine or auramine. The preferred detecting material is, for this method, anti-human IgG conjugated with fluorescein through an isothiocyanate. The product is well known and commercially available.

Basically, the test method of the previous invention comprises the detection of a conjugate formed by reaction between the N.g. produced heat liable antigen and complementary heat stable antibody. Detection is preferably effected utilizing the reaction with an antigen or anti-human IgG labeled with an element or chemical which is detectable by a chemical or physical method. Alternatively, the reaction may be detected by permitting it to take place after the antigen is adsorbed on a carrier. Suitable carriers include, for example, various polymer lactices such as a polystyrene latex, bentonite or charcoal, cholesteroal, lecithin or red blood cells. The particles comprising antigen adsorbed on an adsorbent are then mixed with the sera to be tested and the presence or absence of flocculation of clumping noted. The sensitivity of this procedure may be enhanced by washing the particles to remove unreacted protein followed by the addition of anti-human IgG. Positive reactions give clumps while in negative reactions the antigen coated particles remain homogeneously dispersed.

As stated above, the preferred detection method with suspensions is the fluorescent method. However, the anti-human IgG can also be labeled with a radioactive element or with an enzyme. The radioactive label can be detected by any of the currently available counting procedures. The preferred isotope labels are $^{14}C$, $^{131}I$, $^{=}I$ and $^{35}S$. The enzyme label can be detected by any of the presently utilized colorimetric, spectrophotometric fluorospectrophotometric or gasometric techniques. The enzyme is conjugated to the anti-human IgG by reaction with bridging molecules, such as carbodiimides, diisocyanates, glutaraldehyde and the like. Many enzymes which can be used in these procedures are known and can be utilized. The preferred are peroxidase, B-glucuronidase, B-D-glucosidase, B-D-galactosidase, urease, glucose oxidase plus peroxidase, galactose oxidase plus peroxidase and acid phosphatase.

TAXONOMIC DESCRIPTION OF
ATCC 21823, 21824 AND 21825

Order: Eubacteriales
Family: Neissericeae
Genus: Neisseria
Species: Gonorrhoeae

Morphology: Gram negative spherical or bean shaped diplococci with adjacent sides flattened usually $0.6 \times 1.0 \mu$ and more uniform in size.

Biochemical and Cultural: Aerobic, optimal growth requires 4–10% $CO_2$ and incubation at 36° C.

The cultures grow slowly on chocolate agar producing small, barely visible colonies after 24 hours (0.1 mm in diameter) with typical morphology seen on 48–72 hours cultures. The colonies are small 1.0 mm in diameter, gray white, transparent, smooth, with round entire edge, glistening surface and butyrous consistency. B-1094 produced slightly larger colonies and grows more rapidly.

Oxidase +, catalase +; ferments glucose but not maltose, lactose or sucrose.

Antigenicity: All three isolates share common antigens which are heat labile "L."

Virulence: All three strains were originally isolated from patients with symptomatic gonorrhea.

In the process of the invention the sera to be tested is diluted in physiological saline solution at a dilution of from about 1:2 to 1:1000, heating the suspension to about 56° C. to 65° C. preferably 59° C. for a period of from about 15 to 40 minutes preferably 30 minutes to inactivate heat labile natural antibodies and then incubating the heated serum with an antigen produced from a culture of N.g. The heat labile antigen has not been previously detected or reported. For the agglutination test the preferred ratio is at the lower end of the range or even undiluted. For the radioimmunoassay, the preferred ratio is at the higher end of the scale, and for the fluorescence test the preferred ratio is from 1:10 to 1:40.

For the preparation of the antibody slides of the previously described inventions, fresh isolates of the N.g. organisms are lyophilized or frozen in liquid nitrogen. They are reconstituted as needed and subcultured as needed, on chocolate agar with rabbit blood (Table II) medium. Maintenance cultures in semisolid media (Table III) may be transferred once a month to maintain viability. The cultures are transferred as needed to a suitable growth medium, preferably chocolate agar (rabbit blood) slants, and these are incubated at about 34° C. to 38° C., preferably 35° C. to 37° C. for from about 18 to 24 hours normally in a $CO_2$ (4–10%) atmosphere. The organisms do not grow appreciably at temperatures significantly below 35° C. and die above about 38° C. At periods appreciably below 18 hours the amount of growth is too scarce to be practical, and there is a gradual decline in available antigen after about 24 hours.

Preferably the suspension is checked for purity and typical morphology by Gram staining and streaking on growth medium.

The growth is suspended in physiological saline at a concentration of from about $10^5$ to $10^9$ organisms per ml. For the fluorescence test, the preferred concentration is from $3 \times 10^6$ to $4 \times 10^6$. For the agglutination and enzyme tests, the preferred concentration is of the order of $10^8$ organisms per ml.

A standard antigen slide is a slide preparation where one drop (about 0.50 ml) of a suspension of N.g. organisms in physiological saline at a concentration of $3-4 \times 10^6$ organisms per ml is placed, dried and fixed.

A small drop of the suspension is placed on each end of a cleaned fluorescent antibody slide and smeared with a loop. The slides are air dried, fixed and then rinsed in distilled water to produce a standard antigen slide. The slide is stable after 1 to 3% formalin fixation or without fixing for up to 6 weeks if maintained at about −20° C. They can be lyophilized and will retain their usefulness for as long as 2 to 3 months at room temperature. The preferred fixative for a refrigerator temperature of about 10° C. is one containing 10% formalin in phosphate buffered saline at pH 7.6, 895% ethanol, and glacial acetic acid in the ratio of 10:90:5. With this reagent the fixed suspension will remain stable for an extended period of time, even more than three months. At refrigeration temperatures, the stability may be enhanced by the presence of a dessicant such as anhydrous calcium chloride.

When utilized in the fluorescent process described above, the antibody slides are stained with diluted samples of the serum to be tested. The serum is diluted to 1:10 to 1:40 with physiological saline. The diluted serum is divided into two aliquots of about 0.5 ml each, and one sample is heated, preferably at 59° C. for 30 minutes.

One drop of the heated diluted serum is added to the suspension on one end of the slide, and a drop of the unheated diluted serum is added to the suspension at the other end of the slide. The slide is then incubated for about 15 to 30 minutes in a humid chamber, preferably one that is saturated with water vapor at from about 22° C. to 37° C.

Upon removal from the chamber, the samples are washed thoroughly in buffered saline to remove serum proteins which are not bound to the antigens or cells. A suitable buffer is the standard phosphate buffer at a pH of 7.5 to 7.7. Washing is preferably accomplished by first dipping several times in the buffer solution, then holding in fresh buffer solution for about 10 minutes, and finally rinsing in millipore $H_2O$. The slide is then dried, suitably by gently blotting with an absorbent paper.

The dried smears are stained with fluorescein isothiocyanate conjugated anti-human IgG for about 20 minutes. The working dilutions for particular conjugate will vary from one lot to the other, and are best determined by titration with known controls. The slides are then mounted, suitably in a glycerol-carbonate-bicarbonate buffer at a pH of from about 8.5 to 9.5, preferably 9.0. Any of a number of mounting fluid compositions can be employed, but they should be selected to have a minimum of autofluorescence.

The degree of fluorescence may be determined with a fluorescent microscope, typically a Leitz fluorescent microscope fitted with an HBO-200 light source, a 3-mm BG-12 exiter filter, a BG-38 red excluding filter, an OG-1 ocular filter, a dark field condenser, and a 100 × oil immersion objective.

The fluorescence of the smear stained with the heated serum specimen is compared with the smear stained with the unheated portion of the serum. Specimens that show 1 t 2+ fluorescence or more with the unheated serum with no or insignificant reduction on the heated specimens are considered positive.

Lyophilized products from suspensions of N.g. growth cultures, especially ATCC 21823, 21824 or 21825 are especially valuable sources of antigens. They may be prepared by the following procedure:

A. Prepare concentrated suspensions in sterile milk (100 gr. of skim milk — Baltimore Biological Laboratories — added to 1 l. of water which was preheated to 50° C., sterilize 113° C. to 115° C. for 20 minutes), and then add 5% rabbit or horse blood.

B. To prepare milk suspension, wash culture slant down with 0.5 ml milk using a capillary pipette. Dispense 2 drops culture suspension at the bottom of the prenumbered glass tubes.

C. Dispense no more than 0.05 ml of suspension into the bottom of 6–7 × 100 mm. cottonplugged tubes.

D. Remove cotton plug and insert tube in rubber sleeve of connection to vacuum pump, making sure that:

1. Every plug is discarded directly into container for sterilization.
2. Every tube on any one connection contains some culture.

E. Place tubes in bath of dry ice and 95% ethyl alcohol with tilting motion to deposit some of suspension on glass a few millimeters above major part of material to be dried.

F. Until connected to the manifold of the pump and the pressure is satisfactory for rapid drying, keep cultures in, or so near freezing bath, that no thawing can occur.

The lyophilized products are characterized by the presence of a heat labile antigen which will react with a heat stable N.g. antibody in patients ' sera to form an antigen-antibody complex. They are especially valuable because they can be used in any of the variations of the test procedures described herein. They can, for example, be taken up in physiological saline and the suspension used in the fluorescent procedure described above. They are also valuable in the enzyme and radioactive techniques, as will be readily apparent to those skilled in the art.

The adaptation of the process of the invention to an enzyme testing technique with cell suspensions is accomplished by labeling the anti-human IgG with an enzyme such as horseradish peroxidase. The antigen-antibody conjugate is prepared from a sample of heated serum and antigen suspension as described above. The sample is incubated with the labeled anti-human IgG and washed to remove extraneous protein. The washed product is mixed with a substrate such as o-dianisidine and hydrogen peroxide. After about 3 to 5 minutes the reaction is stopped by the addition of a few drops of 6N sulfuric acid. The optical density is measured at 400nm. Reactive sera is indicated by a higher optical density than similarly treated negative controls.

Other acids can be used to arrest the reaction, for example, hydrochloric acid. In that event, the preferred reading for optical density may be other than 400 nm.

In the radioimmunoassay procedure anti-human IgG or the antigen is labeled with the selected isotope according to standard procedures, reacted with patient serum and the antigen-antibody complex separated and counted using any standard instrument.

The methods of the invention are applicable, as described above, to antigenic cell suspensions. With cell suspensions, the preferred procedure is the fluorescence method which, when utilized as described above, depends upon the morphology of the cells, — as will be recognized by those skilled in the art.

In another, and more preferred, embodiment of the invention, purified antigens or antigenic compositions are employed. With these materials, all of the general methods described above are also applicable. The use of purified antigens or antigenic compositions is preferred over the use of cell suspensions because the results are generally more reproducible and the procedures are more easily automated. Moreover, the fluorescence procedure, when applied to these materials, is not subjective as in the case of cell suspensions, but rather it is objective since the results are determined by comparisons with controls containing known concentrations of antigens and antibodies.

In the presently preferred procedure for purification of the antigen and for the preparation of antigenic compositions, the selected N.g. strains are grown on a suitable media, preferably rabbit chocolate agar. The cell growth is suspended in physiological saline solution and filtered through sterile gauze. During this and all subsequent manipulations involving the antigen or fractions containing the antigen, unless noted otherwise, the solutions, suspensions, etc., are kept cold at about 5° C. to 10° C.

The residue on the filter is washed with physiological saline and centrifuged at about 10,000 RPM for about 15 minutes. The centrifuged material is decanted and the supernatant liquid discarded. The sediment is resuspended in physiological saline, pooled and washed by centrifugation.

The antigen may be extracted with cationic detergents such as sodium lauryl sulfate (SDS), sodium deoxycholate, sodium cholate or similar materials.

The heat labile, species specific antigen of the invention is protein in nature as evidenced by the fact that it is inactivated when incubated with protease enzymes such as pronase, trypsin or chymotrypsin in the usual manner. It is also inactivated by suspension in an aqueous medium at pH values up to 5, but is stable in aqueous mediums at pH values of 7 and above. The antigen becomes more heat stable with increased purification, but is generally inactivated by heating at about 56° C. for 30 minutes in aqueous media. It contains no deoxynucleic or ribonucleic acid, as evidenced by its stability when incubated with the corresponding acidases. It is not affected by lipase or dextranase. It is not a neuramic acid, since it is stable to neuraminidase. Neither is it a cell wall unit (murine), since it is not inactivated by lysosyme.

While the purified antigen can be prepared by the procedures described above, and can be used in the process of the invention, it is not necessary, nor is it preferred to do so. The reason for this is that antigenic compositions containing even relatively high quantities of impurities such as extraneous protein can be used.

The antigenic activity of a particular composition can be defined in terms of antigen units by reference to the standard antigen slide as defined above. The method of determining antigen units will require some explanation. It is based on the ability of a particular composition to inhibit the preferred fluorescent test which is used with cell suspensions, and is described in detail above.

As described above, the fluorescent test with cell suspensions depends upon the morphology of the cells. More particularly, it depends upon the morphological localization of the antigen on the intact cell. Optimum conditions for the test prevail when the complete cell is intact. During the course of purification in accordance with the invention, more and more antigen is cleaved from the cells. The compositions thus become less and less suitable for the type of fluorescent testing which depends upon cell morphology.

In the initial stages of purification, there will be relatively large amounts of protein, for example, cellular debris, which is not antigenic in nature in the compositions. This material does not contribute to the antigen unit values. With increasing purification, the extraneous protein is removed and the antigen unit values increase rapidly.

With careful purification, it is possible to obtain products with antigen unit values of 10-20,000 units per mg. of protein, or even higher. However, products with values of at least 100 can be used in fluorescent testing, enzyme testing, radioimmunoassay and agglutination procedures to determine the presence of N.g. antibodies in human sera. It is preferred, however, that the values be at least 1000.

The following definitions will be helpful in understanding this aspect of the invention:

Conjugate Unit (C.U.)

This is the highest dilution of fluorescein conjugated anti-human IgG which when added in aliquots of 0.05 ml to a standard antigen slide preparation stained with excess specific antibodies will give a 4+ fluorescence.

Antibody Unit (Ab.U.)

It is the highest dilution of heat inactivated serum which gives a 4+ fluorescence when used to stain standard antigen slide and counter stained with fluorescein conjugated anti-human IgG appropriately diluted to contain 2 C.U./0.05 ml.

Antigen Unit (Ag.U)

One Antigen Unit (Ag.U) is defined as that amount of a whole, partially purified, or pure antigen preparation, expressed as $\mu g$ protein, which when allowed to react with heat inactivated serum diluted to contain one Ab.U./0.05 ml will absorb this unit of activity and when this adsorbed serum is used to stain the standard antigen slide and counter stained with fluorescein conjugated anti-human IgG appropriately diluted to contain 2 C.U./0.05 ml will give fluorescence of shadow to 1+. An antigen unit is the minimum amount of material which will absorb one antibody unit.

It will be appreciated that the purity of an antigen proteinaceous preparation is directly proportional to the number of antigen units per mg. of protein.

The antigen compositions of the invention can be used in all of the tests described above in connection with cell or organism suspensions. The procedures will be generally the same. For example, the antigen composition can be reacted with the N.g. antibody in test sera on a slide, and the resulting complex incubated with IgG labeled with a fluorescent chemical. Alternatively, the IgG may be labeled with any of the enzymes or isotopes mentioned above. The procedure for the agglutination test described above is the same, except that the suspensions are replaced with purified antigens or antigenic compositions.

It has been observed that the antigens or antigenic compositions of the invention are particularly useful when conjugated or adsorbed on particulate carriers or substrates. Such materials do not affect the antigen-antibody reaction. Neither do they affect the subsequent reaction with the labeled compound. Any of a very wide variety of carriers can be employed, including polymeric materials such as polystyrene, inorganic materials such as glass, silica, bentonite or charcoal, and cellulosic materials such as Sepharose Sephadex or cellulose. Biological carriers such as red blood cells may also be employed.

For the conjugation of a specific N.g. antigen to non-antigenic carriers, equal volumes of the partially purified or pure antigen preparations containing at least 100 Ag.U./mg of protein and the selected carrier, for example, DEAE-cellulose in 0.1 m phosphate buffer at pH 8 are mixed and refrigerated overnight. The particles are recovered by filtration and washed with additional buffer solution, for example, 0.3 m phosphate buffer at pH 7.0, and again with 0.1 m phosphate buffer at pH 7 with 1% albumin. The washed conjugate is resuspended in 0.1 m phosphate buffer at pH 7 with 1% albumin in a volume equal to the volume of the original antigen solution.

The antigen-carrier conjugate may be used in enzyme immunoassay or radioimmunoassay in the manner described above. It has been observed that when these conjugates are employed in the testing procedures there is less background interference in the reading of the testing instruments with resulting better differentiation between positive and negative tests.

The following example illustrates the process of one aspect of the previous invention.

INDIRECT IMMUNOFLUORESCENT ANTIBODY TEST

Preparation of the Antigen

1. Fresh isolates of *N. gonorrhoeae* with appropriate antigen profile or a lyophilized subculture of the standard strains (B-370, B-585 or B-104) are subcultured to maintenance medium (Table III). The cultures are maintained at 37° C. in a 4-10% $CO_2$ atmosphere and subcultured to fresh maintenance medium once a month.
2. The strains are subcultured as needed to freshly prepared chocolate agar slants (rabbit blood) (Table II).
b 3. The slants are incubated at 36° C. for 18-24 hours and the growth is suspended in physiological saline and adjusted to 3-4 × $10^6$ organisms/ml.
4. A small drop of the suspension is placed on each end of an alcohol cleaned fluorescent antibody slide and smeared with a loop.
5. Slides are air dried and fixed in 1% formalin for 10 minutes.
6. Slides are rinsed 10 times in distilled water, air dried and stored at −20° C. until needed.

Preparation of the Patient's Serum

1. Dilute patient's serum 1:10 in physiological saline.
2. 0.5 ml. of the 1:10 dilution is heated for 30 minutes in a 59° C. water bath.

Staining

1. Slides are taken out of the freezer 10-15 minutes before use and labelled with patient's name or number.

2. Add one drop of heated diluted serum to one end of the prepared antigen slides and one drop of the unheated serum to the other end.
3. Allow to incubate at room temperature for 20 minutes in a humid chamber.
4. Wash 10 times rapidly in 0.1 M phosphate buffered saline pH 7.6.
5. Wash for 10 minutes in a fresh bath of the same buffer.
6. Rinse 10 times in distilled water and gently blot dry.
7. Stain with working dilution of fluorescein isothiocyanate conjugated anti-human immunoglobulin G for 20 minutes followed by a washing cycle as before (steps 4 to 6).
8. Mount the slides in a glycerol-carbonate bicarbonate buffer pH 9.0.

Readings

The slides are examined with a fluorescent microscope fitted with an HBO-200 light source, 3 mm BG-12 exciter filter, a BG-38 red excluding filter, and OG-1 ocular filter, a dark field condenser, and a 100 × oil immersion objective.

Interpretation of Results

The degree of the peripheral fluorescence of the bacterial cells in the smear stained with the heated serum specimen is compared with the smear stained with unheated serum. Specimens that show 1–2+ fluorescence or more with no or insignificant reduction after heating, are considered positive and interpreted to indicate current or recent past infection.

The following example illustrates the preparation of purified N.g. antigenic compositions.

PREPARATION OF ANTIGENIC COMPOSITIONS

The cell growth from step 2 of the illustrative procedure shown above is harvested and suspended in physiological saline solution. It is then filtered through chessecloth at a temperature of 5°–10° C., which temperature is maintained throughout subsequent manipulations. The residue on the filter is washed twice with physiological saline solution and the filtrate centrifuged at 10,000 rpm for 10 minutes. The sediment is resuspended in physiological saline and washed once by centrifugation. The sediment containing the antigen is weighted to calculate the wet weight.

A total of 6.0 ml. of 0.3% SDS in physiological saline is added to the precipitate from the centrifugation per gram of wet weight of bacterial sediment, and the mix is incubated at room temperature for 10 minutes. The mix is centrifuged at 10,000 rpm for 10 minutes and the supernatant collected. The sediment is treated with 6.0 ml/gm. of 0.1% SDS in physiological saline. The mix is incubated at room temperature for 10 minutes, centrifuged as before, and a second supernatant collected. The two supernatants are recentrifuged to remove any cells or large fragments and pooled.

At this point, the antigen unit value is 100–200 Ag.U./mg. of protein.

The pooled supernatant is concentrated using Amicon Membrane XM100 and then column chromatographed over Sepharose 4B and eluted with 0.002 molar phosphate buffer at pH 7.6. Appropriate fractions (usually b 4–10 ml) are collected and the protein concentration monitored by the Lowry technique. The antigen composition with the best Ag.U. value is found in the first peak which is made up of 5–10% of the protein. With fresh preparations, the value is from 1000–2000 Ag.U./mg.

The tables referred to above are given below.

TABLE I

FERMENTATION MEDIUM

Starch gelatin agar, infusion-free, with indicator and carbohydrate (for *Neisseria gonorrhoeae* and *Neisseria meningitidis*)

| | |
|---|---|
| Agar | 3 grams |
| Gelatin | 10 grams |
| Sodium chloride | 5 grams |
| Peptone (Difco proteose No. 3) | 10 grams |
| Starch, soluble, powdered | 5 grams |
| Water to Make | 1000 grams |
| Phenol red, 0.02 percent | 30 ml. per kg. |
| Carbohydrate (Sucrose, Glucose or Maltose) | 10 grams per kg. |

Dissolve the agar in half the water by autoclaving; the gelatin, salt, peptone, and starch in the remainder with heat. Combine and make up to total weight. Adjust pH to 7.4–7.6. Filter through cotton. Weigh the filtrate recovered and add the indicator and carbohydrate. Dispense 2.5 ml. amounts in 11 by 75 mm tubes and autoclave at 115° C. for 12 minutes. Trim the plugs and seal with paraffin.

TABLE II

GROWTH MEDIUM

Glucose agar, infusion-free, with coagulated blood (for *Neisseria gonorrhoeae* and *Neisseria meningitidis*)

| | |
|---|---|
| Agar | 15 grams |
| Sodium | 5 grams |
| Disodium phosphate, $Na_2HPO_4$ | 5 grams |
| Peptone, (Proteose peptone No. 3) | 20 grams |
| Glucose | 0.5 grams |
| Distilled water to make | 1000 grams |
| Rabbit blood, defibrinated, sterile | 10 ml. per 100 ml. |

Dissolve the agar in half the water by autoclaving; the salts, peptone, and glucose in the remainder with heat. Combine and make up to 1 kg. and adjust pH to 7.4–7.6. Dispense 1500 ml. amounts in 3L gauged neck flasks. Autoclave thirty minutes. Store.

As required, melt the agar base. Admix the blood aseptically 15–20 ml. amounts in glass-covered Petri plates. Deliver without incubation.

TABLE III

MAINTENANCE MEDIUM

| | |
|---|---|
| Beef-infusion agar with ascitic fluid | |
| Beef infusion, concentrated | 500 grams |
| Agar | 5 grams |
| Sodium chloride | 5 grams |
| Peptone | 10 grams |
| Water | 500 grams |
| Ascitic fluid, sterile | an equal volume |

Dissolve the agar in the water by autoclaving, and the peptone and salt in the infusion. Combine. Make up to total weight. Adjust pH to 7.5 with 1N NaOH. Filter by asperation. Usually dispense 400 ml. amounts in 2 liter flasks and autoclave 30 minutes. Store. Melt the agar base and cool to 50° C.

Warm the ascitic fluid to 50° C. and combine aseptically. Mix well and dispense with aseptic precautions 4–7 ml. amounts in 15 by 125 mm tubes. Cover the medium aseptically with about 4 ml. of sterile mineral oil. Cool in an upright position. Incubate 48 hours at 35°–27° C. and 96 hours at 20°–27° C. Inspect and store.

TABLE IV
SUBSTRATE FOR PEROXIDASE TEST a) Dilute 3% hydrogen peroxide solution with water to make a one to one hundred dilution.
b) Dilute the solution with phosphate buffer (0.01 molar at pH 7) to another one to one hundred dilution.
c) To 24 ml. of the thus diluted hydrogen peroxide, add 0.2 ml of a 1% solution of O-anisidine in methanol.

TABLE V
CHARCOAL GROWTH MEDIUM*

| | |
|---|---|
| Difco GC medium base | 36 g |
| Isovitalex | 10 ml |
| Fischer Scientific neutral activated decolorizing carbon | 5 g |
| Distilled water | 1000 ml |

*Developed by Dr. Hideo Kusamo of the Division of Laboratories and Research as a substitute for the rabbit chocolate agar.

A large proportion of this specification has been devoted to a complete description of the previously described invention. The reason for this is that, although the invention described and claimed herein is a completely new invention, it is useful as an improvement of the earlier invention. The various techniques used to detect the antigen-antibody complex applicable to the earlier invention are also application to this invention. The N.g. antigenic compositions of the earlier invention may also be employed in connection with this invention. The previously defined antigen slides can be employed, although because of the improved sensitivity of the process of this invention, it is not essential that the slide be prepared with two antigen compositions per slide.

It will be seen that an important step in the various tests described above is that the sera to be tested be heated at 56° C. to 65° C. to inactivate cross-reacting heat labile antibodies. It has now been discovered that one class of cross-reacting antibodies survives the heat treatment. This class is antibodies cross-reactive with N.m. These give rise to false positive reactions since they cross react when tested with the N.g. antigenic compositions described above.

Actually, the number of false positive reactions associated with the earlier test procedures is well within the limits acceptable in a voluntary screening program. However, the psychological trauma associated with false positives, especially when the individual is submitting to the test as a legal requirement for marriage, demands that the number of false positives be reduced to a minimum, even if there is some loss in the sensitivity of the test.

The fact of the cross-reactions was discovered utilizing sera known to contain either N.g. antibodies, N.m. antibodies or both in tests with N.g. antigenic compositions prepared as described above or N.m. antigenic compositions prepared generally as described above. It was observed that some of the antibodies which react with N.m. would react with N.g. antigens giving a positive result irrespective of whether the patient was infected with gonorrhea or completely free of such infection as evidenced by bacteriological tests and clinical findings.

Accordingly, N.m. antigenic compositions, described herein as N.m. sorbent compositions were prepared for initial reactions with the sera to be tested. By this procedure, any cross-reacting antibodies in the sera would be conjugated or absorbed by the sorbent composition. The resulting mixture of sorbent and sera could be incubated with an N.g. antigenic composition prepared as described above with the danger of false positive reactions reduced to a minimum.

The N.g. antigenic compositions used in the practice of this invention can be any of those, the preparation of which is described above. Preferably the N.g. antigen composition will have an N.g. antigen unit value of at least 100 Ag.U./mg. of protein. Ideally the value will be 1000 or more. Such compositions may be on antigen slides as described above; they may be cellular suspensions or they may be lyophilized compositions.

Similarly, the N.m. sorbent compositions may be cellular suspensions; they may be on a slide; they may be lyophilized or they may contain the antigen absorbed to any of the carriers mentioned above such as polystyrene, glass, silica, bentonite, charcoal, Sepharose or Sephadex.

For convenience the compositions may be defined in terms of sorbent units. Compositions containing from 50 to 10,000 sorbent units per mg. of protein are useful in the practice of the invention. The sorbent unit (SU) is defined as that amount of whole, partially purified, or pure N.m. antigen preparation, expressed as mg. protein, which when allowed to react with heat inactivated serum diluted to contain one antibody unit of each of N.g., and the appropriate serogroups of N.m., will absorb the antibodies reactive with N.m. but not N.g.

When this absorbed serum is used to stain N.m. slides and counterstained with fluorescein conjugated antihuman IgG appropriately diluted to contain 2 conjugate units/0.05 ml., it will give a fluorescence of shadow to 1+ but when the same absorbed serum is used to stain N.g. slides, a fluorescence of 3–4+ should be observed.

The optimum dilution of the sorbent would vary according to the procedure used, e.g. radio immunoassay, enzyme immunoassay, agglutination or immunofluorescence absorption test. The range from 0.1 to 100 sorbent units is most useful. In case of the last-mentioned procedure, best results were obtained with dilution containing 0.5 unit of sorbent/0.2 ml. to be mixed with 0.2 ml of heat inactivated patient's serum.

Sorbent compositions can be prepared to contain antigens from one or all of the serogroups. If the composition is to contain antigens from more than one group, it is best to prepare them separately by the procedure generally described above and then mix them in the appropriate ratio to produce the desired working sorbent.

As is known, infections attributed to one or more specific serogroups are more or less prevalent in a specific geographical area. Thus in northeast United States infections associated with serogroups A, B and C are more common than those associated with other serogroups. It is a special advantage of this invention that N.m. antigenic sorbent compositions can be tailored to the need of a specific area. Thus the compositions may contain one or a plurality of antigens from separate groups.

For uniformity the concentration of each serogroup in a final sorbent composition is about 0.3 to 0.6 SU/0.2 ml of diluent.

Test results obtained by the immunofluorescent technique with over 500 sera including sera from individuals positive and negative by clinical and bacteriological criteria have established that the number of false positives may be reduced by as much as 58% (2+ or higher were reduced 42%) and the borderline reactions were reduced 75% compared with the previously described procedure. This is a remarkable result considering that the sensitivity of the previously described test has been found to be 81% and the specificity is 93% (7% false positives and 9-10% borderline reactions) in the target population of asymptomatic women (field evaluation covering 11,800 women).

The following non-limiting examples are given by way of illustration only.

EXAMPLE I

N.M. SORBENT COMPOSITION

I. Sorbent Composition of *N. menigitidis* serogroup A

A. Preparation of the sorbent

1. *N. meningitides* strains representing the standard reference strains (for the different serogroups (ATCC 13077, 13090, 13102, 13113) as well as any of the newly reported serogroups which might be prevelant in the community) is subcultured from maintenance medium (Table III), lyophilized state, or from cultures kept frozen in liquid nitrogen to a suitable culture medium preferably chocolate agar plates (rabbit blood) (Table II).

2. Typical colonies are used to inoculate chocolate agar slants.

3. The slants are incubated for 18–24 hours at 36° C and the growth checked for purity by Gram stain.

4. Pure cultures are examined for the presence of cross reacting antigen(s) as follows:

i. Cells are suspended in a medium containing 2% sucrose (w/v) and 0.2% gelatin (w/v) in physiological saline, clumps gently disrupted and the density of the suspension adjusted visually to that equal to a standard density $1 \times 10^8$ cells/ml.

ii. A small drop of the suspension is placed on clean microscope slide (10 spot masked slides) and spread with 5 mm loop.

iii. The slides are air dried and fixed in 2% buffered formalin for 10 minutes, washed by dipping in distilled water three times, rinsed in a fresh water bath for four minutes, drained and blotted dry.

iv. A known positive patient's serum is used as a control. The working dilution is that which gives 3–4+ fluorescence with a good N.m. and N.g. antigen slide.

v. The control serum is diluted to the appropriate working dilution and heated for 30 minutes in a 59° C water bath.

vi. One drop of the heated serum is applied to each antigen spot and the slide incubated at room temperature for 20 minutes in a humid chamber.

vii. The slides are washed 10 times rapidly in 0.1 M phosphate buffered saline pH 7.6, placed in a fresh PBS for 10 minutes, rinsed 10 times in distilled water, then gently blotted dry.

viii. One drop of the working dilution of fluorescein isothiocyanate conjugated anti-human IgG is placed on each spot for 20 minutes followed by washing and drying as before (steps vi – vii).

ix. Slides are mounted in glycerol-carbonate bicarbonate buffer pH 9.0 and examined with a fluorescent microscope. The microscope used in our study is a Leitz ultra-violet microscope (orthoplan) fitted with a Ploem reflected light system, HBO-200 light source, 3mm BG-470 exciter filter, 2 BG-38 red excluding filters in the lamp house, and a K490 exciter filter and one 530 ocular filter in the Ploem attachment. The slides were examined under 100× oil immersion objective (1250×). Similar results could be obtained using the transmitted light system and the filter combination described before (page 19).

x. Cells showing 3–4 homogenous, peripheral fluorescence are considered usable and the original slants subcultured.

5. Cells with cross reacting antigens are subcultured on charcoal growth medium (Table V) in 29 oz. tissue culture bottles and incubated for 18–24 hours.

6. The growth from the bottles is harvested and if pure by Gram stain, is used to inoculate heavily large trays containing the same charcoal medium.

7. After 18–24 hours incubation the growth from the trays is harvested in physiological saline filtered through sterile gauze and centrifuged at 5,000 rpm for 10 minutes. The pellet is re-suspended in 0.3% sodium dodecyl sulfate (SDS) in physiological saline (4 ml/g of wet weight). The suspension is homogenized gently for 10 minutes at room temperature and centrifuged at 15,000 rpm for 10 minutes. The supernatant fractions are pooled and the cell pellet re-extracted with 0.5% SDS as before.

8. The pooled extracts are concentrated by Amicon XM-50 cell using Amicon membrane XM100A.

9. The concentrated extract is chromatographed on Sepharose 4B column and eluted with 0.002 M sodium phosphate buffer pH 7.6.

10. The void volume is concentrated with Ficol to 1/10 its volume, frozen in liquid nitrogen, thawed and incubated for three hours at room temperature with EDTA and Triton X-100 at final concentration of 10 mM EDTA and 1.5% Triton X-100.

11. The mixture is centrifuged at 100,000 × g for 1 hour.

12. The supernatant is refered to as the soluble antigen and was used as sorbent without further purification after determining the protein concentration.

B. Determination of the sorbent units and working sorbent

1. Different dilutions of the sorbent are prepared to contain 10 to 0.1 μg protein/0.2 ml of saline.

2. 0.2 ml of heat inactivated control serum diluted to contain one N.g. antibody unit, one N.m. (specific group) antibody unit/0.05 ml, is mixed with 0.2 ml of the appropriate dilution of the sorbent.

3. Incubate at room temperaure for 1 hour.

4. This "sorbed" serum specimen together with a (un-absorped) control made up of similarly treated 0.2 ml of saline rather than sorbent are used to stain N.g. and N.m. slides as described before (Steps $4_{vi}$ to $4_{ix}$).

5. The lowest concentration of sorbent which will reduce the fluorescence to shadow to 1+ on N.m. slides compared to 3–4+ fluorescence with the un-absorped control but does not reduce the fluorescence on the N.g. slide to any significant degree, is considered to be equal to one sorbent unit and is expressed as μg protein. The activity of the sorbent would be equal to 1,000((1 (SU) as μg protein).

6. The working sorbent mixture would be the adjusted dilution equivalent to 0.05 SU/0.2 ml saline.

II. Sorbent Composition of *N. meningitidis* Serogroup B

Same as 'I', but the *N. menigitidis* strain is N.m. serogroup B, reference strain ATCC 13090.

III. Sorbent Composition of *N. menigitidis* Serogroup C

Same as I, but the *N. menigitidis* strain is N.m. serogroup C, reference strain ATCC 13102.

IV. Sorbent Composition of *N. menigitidis* Serogroup D

Same as I, but the *N. menigitidis strain is N.m. serogroup D, reference strain ATCC* 13113.

V. Sorbent Composition of *N. menigitidis* Serogroup X

Same as I, but the *N. menigitidis* strain is N.m. slaterus serogroup X.

VI. Sorbent Composition of *N. menigitidis* Serogroup Y

Same as I, but the *N. menigitidis* strain is *N.m. slaterus* serogroup Y.

VII. Sorbent Composition of *N. menigitidis* Serogroup Z.

Same as I, but the *N. menigitidis* strain is *N.m. slaterus* serogroup Z.

VIII. Working Sorbent Composition

1. The sorbent mixture is prepared according to the prevelant *N. menigitidis* in the community although a universal mixture is feasable if highly active sorbent preparations 5,000–10,000 SU/mg protein were used.

2. The working mixture is prepared by mixing equal volumes of the individual sorbents desired each calculated to contain 0.5 SU. The volume used is calculated as follows:

$$V = 0.2/N$$

V — Volume of each sorbent
N — Number of individual sorbents used

EXAMPLE II

FLUORESCENT GONORRHEAL TEST-ABSORPED (FGT-ABS)

Preparation of the Antigen

1. Fresh isolates of N.g. with appropriate antigen profile or a lyophilized subculture of the standard strains (ATCC 21823, 21824, and 21825) are subcultured to maintenance medium (Table III) or suspended in proteose-peptone broth with 10% DMSO and frozen in liquid nitrogen (−176° C) or lyophilized.

2. The strains are subcultured as needed to freshly prepared chocolate agar plates (rabbit blood) (Table II).

3. The plates are incubated for 24 hours at 36° C in a 4–10% $CO_2$ atmosphere.

4. Typical colonies are used to inoculate chocolate agar slants.

5. The slants are incubated for 18–24 hours and pure cultures are used.

6. Cells are harvested in a suspending medium containing 2% sucrose (w/v) and 0.2% gelatin (w/v) in physiological saline, any clumps are gently disrupted and the density of the suspension adjusted visually to that equal to a standard density of $1 \times 10^8$ cells/ml.

7. A small drop of the suspension is placed on a circumscribed area on clean microscopic slides and spread using 5 mm loop. (Automatic applications using a dispenser is possible.)

8. The slides are air dried and fixed in 2% buffered formalin for 10 minutes, washed by dipping in distilled water three times, rinsed in a fresh water bath for four minutes, drained and blotted dry.

9. Each lot is examined with a known positive control which gives 4+ fluorescence at 1:10 dilution and diluted to give 1–2+ fluorescence with good slides. A negative control is included. Only lots that give the expected positive, borderline, and negative reactions are considered satisfactory and used.

10. Satisfactory lots are stored at −20° C in closed containers which contain calcium chloride crystals. Slides were prepared as needed, but one lot used to test shelf life is still satisfactory after 9 months.

Preparation of Patient's Serum

1. Dilute patient's serum 1:5 in physiological saline.

2. 0.5 ml of the dilution is heated for 30 minutes in a 59° C water bath.

3. 0.2 ml of the heat inactivated serum is mixed with 0.2 ml of the sorbent containing 0.5 SU of sorbent A and 0.5 SU of sorbent C.

4. Incubate at room temperature for 1 hour.

Staining

1. Slides are taken out of the freezer 10–15 minutes before use and labelled with patient's name or number.

2. One drop of the sorbed serum is applied to the appropriately marked corresponding spot on the multispot slides.

3. Incubate at RT for 20 min. in a humidity chamber.

4. Wash 10 times rapidly in 0.1 M Phosphate buffered saline (PBS) pH 7.6, place in a fresh PBS bath for 10 minutes, rinse 10 times in distilled water, then gently blot dry.

5. Stain with working dilution of fluorescein isothiocyanate conjungated anti-human immunoglobulin G for 20 minutes, followed by a washing cycle as described in step 4.

6. Mount the slides in a glycerol-carbonate-bicarbonate buffer pH 9.0.

Reading

The slides are examined with a fluorescent microscope fitted for transmitted or reflected light systems.

1. Transmitted light — The fluorescent scope may be fitted with any light source with an emission spectrum which includes the fluorescene isothiocyanate excitation spectrum. A good example is Mercury bulb HBO-200. The microscope is fitted with 3 mm BG-12 exciter filter, a BG-38 red excluding filter, an OG-1 ocular filter, a dark field condenser, and 100× oil immersion objective (1000×).

2. Reflected light — A fluorescent microscope fitted with any suitable light source. Our scope was fitted with HBO-200 light source, 3 mm BG-470 exciter filter, two BG-38 red excluding filters, K490 exciter filter, and 530 Ocular filter. The slides were examined under 100× oil immersion objective (1250×).

Interpretation of Results

The degree of peripheral fluorescence of the bacterial cells were graded from shadow (S) to 4+. Specimens that show 1–2+ fluorescence or more are considered positive and are interpreted to indicate current of recent past infection with *N. gonorrhoeae*.

EXAMPLE III

ENZYME-LINKED IMMUNOASSAY

A. Insoluble protein-bacterial gel

Preparation of the Antigen

1. Fresh isolates of N.g. with appropriate antigenic profile or subcultures from standard strains (ATCC 13077, 13102, 13113) are maintained in maintenance medium (Table III), lyophilized, or frozen to chocolate agar slants (rabbit blood) (Table II).
2. 18–24 hour growth is harvested in physiological saline and adjusted to about 3–4 × $10^8$ colony firming units (CFU)/ml.
3. Rabbit IgG in 0.1 m Phosphate buffered pH 7.0 is added to the bacterial suspension to final concentration of 50 mg/ml.
4. Add aqueous solution of 2.5% gluteraldehyde dropwise with gentle sitrring to a final concentration of 10 mg gluteraldehyde per 100 mg protein in solution.
5. Leave at room temperature for 1 hour.
6. Disperse the insoluble protein-bacterial gel in 0.2 M phosphate buffered saline pH 7.2, centrifuge at 3000 rpm for 15 minutes.
7. Repeat step 6 two times.
8. Resuspend the protein-bacterial gel in a volume of 0.2 M phosphate buffered saline pH 7.2 four times the volume of the rabbit protein added in step 3.
9. Dispense the suspension in 0.25 ml aliquots and store in refrigerator until used.

Preparation of Patient's Serum

1. Dilute patient's serum in 0.2 M phosphate buffered saline pH 7.2 (PBS) 1:5, 1:50, 1:500.
2. Heat the different dilutions for 30 minutes in a 59° C water bath.
3. Add 0.2 ml of heat inactivated serum to 0.2 ml of sorbent in PBS.
4. Incubate at room temperature.

Procedure

1. Add 0.25 ml of each sorbed and heat inactivated dilution of patient's serum to 0.25 ml of antigen and mix.
2. Incubate at 37° C for 15 minutes in water bath.
3. Centrifuge at 3,000 rpm for 5 minutes and discard the supernatant.
4. Wash the pellet 2 times with 5 volumes of PBS.
5. Add 0.1 ml of working dilution of horseradish peroxidase (HRP) conjugated anti-human immunoglublin G.
6. Incubate at 37° C for 15 minutes in a water bath.
7. Add 5.0 ml PBS, centrifuge and wash the pellet as described in step 4.
8. Add 3.0 ml of substrate (Table IV) and mix by shaking.
9. After 5 minutes, the reaction is stopped by adding one drop of 6N sulfuric acid.
10. The O.D. is measured at 400 mm.

Interpretation

Reactive sera are indicated by comparison with a standard curve prepared with known positives and negative sera.
Controls (should be added with each batch)
a. Positive controls
b. Negative controls
c. Weakly positive (borderline reactive controls)
d. Antigen control
e. Substrate control
f. Enzyme controls B. Filter Test Preparation of the Antigen 1. Cell suspension is prepared as in 'A', steps one and two.
2. Suspension is stored in refrigerator until used.

Preparation of Patient's Serum

As in 'A'.

Procedure 1. 0.2 ml of the bacterial suspension is mixed with 0.2 ml of the sorbed serum in a dispensable tube.
2. Incubate at 37° C for 15 minutes.
3. Wash three times with 5.0 ml of PBS.
4. Resuspend the cell suspension in 1.0 ml of PBS and place it on a disposable filter and remove the buffer by suction.
5. Add 0.1 ml of working dilution of horseradish peroxidase conjugated anti-human Immunoglobulin G.
6. Incubate at 37° C for 15 minutes.
7. Wash with three 5.0 ml of PBS and check the last washing for enzyme activity. Washing should be repeated if enzyme is detected in the washing.
8. Add 1.0 ml of substrate.
9. Reactive sera gives reddish-brown pigmentation of the filter.

EXAMPLE IV

CONJUGATION TO NON-ANTIGENIC CARRIER

A. Sorbent-Cellulose (S-C)

1. Equal volumes of sorbent A solution containing a minimum of 100 SU/mg of protein and DEAE-cellulose in 0.1 M phosphate buffer at pH 8, mixed, and left standing overnight in the refrigerator. The mixture is filtered and washed three times with an equal volume of 0.3 M phosphate buffer at pH 7.0 followed by an additional three washings with equal volumes of 0.1 M phosphate buffer pH 7.0 with 1% albumin.
2. The washed sorbent-cellulose (SC) conjugate is resuspended in 0.1 M Phosphate buffer at pH 7.0 with 1% albumin to a volume equal to that of the original solution.
3. The sorbent activity of the conjugate is determined as described before (Example IB) and diluted in 0.1 M Phosphate buffer pH 7.0 with 1% albumin to contain 5 SU/ml.
4. 0.5 ml of the S-C is mixed with equal volume of patient's serum and incubated at room temperature for 1 hour.
5. Centrifuge at 3,000 rpm for 10 minutes and use the supernatant (sorbed serum).
6. The sorbed patient serum may be used in various agglutination, radio-immunoassay, and immunofluorescent tests.

B. Sorbent-Sepharose (S-S)

1. Mix 1 gram of cyanogen bromide activated sepharose IV particles (CNB-Sepharose activated — Pharmacia Fine Chemicals) with 5 ml portions of $10^{-3}$ M HCl.
2. Pour the fractions containing at least 100 SU/mg of protein onto the Sepharose bed and recycle filterator several times until the protein is adsorped, maintaining at all times a temperature of 5°–10° C.

3. Block any remaining active sites on the sepharose by adding 5–10 ml of 0.5% Bovine Serum Albumin in 1 M glycerine buffer pH 8.2, recirculate filterate overnight by continuous flow peristaltic pump.

4. Let filtrate drain out and resuspend the particles in 10 ml saline solution. Centrifuge at about 10,000 rpm for 10 minutes, decant and discard supernatant liquid.

5. Repeat washing as in step 4 and recover precipitate.

6. Suspend sorbent particles (S-S) in about 10 ml of saline solution.

7. The sorbent activity of the conjugate is determined as described before and diluted to contain 5.0 SU/ml.

8. 0.5 ml of S-S is mixed with equal volume of patient's serum and incubated at room temperature for one hour.

9. Centrifuge at about 5,000 rpm for 10 minutes and take the supernatant (i.e., sorbed serum).

10. The sorbed serum may be used in various agglutination, radio-immunoassay and/or immunofluorescent tests.

What is claimed is:

1. A serological method for determining the presence of *Neisseria gonorrhoeae* antibodies in human serum which comprises heating the serum at about 56° C. to 65° C. for from about 15 to 40 minutes, the serum being undiluted or diluted with physiological saline at a dilution up to about 1:1000; adding the serum to about an equal volume of *Neisseria meningitides* sorbent composition containing from 0.1 to 100 sorbent units of *Neisseria meningitides* antigen to remove cross reacting antibodies and thereafter mixing and incubating resulting mixture with a composition containing a heat labile *Neisseria gonorrhoeae* antigen produced from a culture of *Neisseria gonorrhoeae* antigen to form *Neisseria gonorrhoeae* antigen-antibody conjugate when said antibodies are present and detecting the presence of such conjugate.

2. A method as in claim 1 wherein the *Neisseria gonorrhoeae* antigen composition is a cellular suspension.

3. A method as in claim 1 wherein the *Neisseria gonorrhoeae* antigen composition has an antigen unit value of at least 100 Ag.U/mg. of protein.

4. A method as in claim 3 wherein the value is at least 1000.

5. A method as in claim 1 wherein the *Neisseria gonorrhoeae* antigen is conjugated to a carrier and the conjugate is detected by an agglutination test procedure.

6. A method of claim 1 wherein the *Neisseria gonorrhoeae* antigen-antibody conjugate is reacted with labeled anti-human IgG and detected as labeled.

7. A method as in claim 6 wherein the anti-human IgG is labeled with a chemical which fluoresces when exposed to ultraviolet light.

8. A method as in claim 7 wherein the chemical is selected from the group consisting of fluorescein, rhodamine and auramine.

9. A method as in claim 6 wherein the anti-human IgG is labeled with a radioactive element.

10. A method as in claim 9 wherein the radioactive element is selected from the group consisting of $^{14}C$, $^{131}I$, $^{125}I$, and $^{35}S$.

11. A method as in claim 1 wherein the heated labile *Neisseria gonorrhoeae* antigen is labelled with a radioactive element.

12. A method as in claim 6 wherein the anti-human IgG is labeled with an enzyme.

13. A method as in claim 12 wherein the enzyme is peroxidase, B-glucuronidase, B-D-glucosidase, B-D-galactosidase, urease, glucose oxidase plus peroxidase, galactose oxidase plus peroxidase, and acid phosphatase.

* * * * *

UNITED STATES PATENT OFFICE
CERTIFICATE OF CORRECTION

Patent No. 4,029,756           Dated June 14, 1977

Inventor(s)   Hassan A. Gaafar

It is certified that error appears in the above-identified patent and that said Letters Patent are hereby corrected as shown below:

Column 1, line 42, "sorben" should read -- sorbent --.

Column 2, line 46, "of", second occurrence, should read -- or --.

Column 2, line 57, "=I" should read -- $^{125}I$ --.

Column 8, line 7, after "Sepharose" insert a comma (,).

Column 9, lines 40-41, "chessecloth" should read -- cheesecloth--.

Column 1, line 61, "in" should read -- is --.

Signed and Sealed this

Sixteenth Day of May 1978

[SEAL]

Attest:

RUTH C. MASON
Attesting Officer

LUTRELLE F. PARKER
Acting Commissioner of Patents and Trademarks